US009097663B2

(12) United States Patent
Updyke et al.

(10) Patent No.: US 9,097,663 B2
(45) Date of Patent: Aug. 4, 2015

(54) GEL ELECTROPHORESIS, IMAGING, AND ANALYSIS METHODS, DEVICES, SYSTEMS, AND MATERIALS

(71) Applicant: LIFE TECHNOLOGIES CORPORATION, Carlsbad, CA (US)

(72) Inventors: Timothy Updyke, Temecula, CA (US); Paul Predki, Carlsbad, CA (US); Evangeline Gonzalez, Poway, CA (US); Randall Lowe, Oakland, CA (US); Tad Simons, Palo Alto, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 0 days.

(21) Appl. No.: 13/717,650

(22) Filed: Dec. 17, 2012

(65) Prior Publication Data

US 2013/0175172 A1    Jul. 11, 2013

Related U.S. Application Data

(63) Continuation of application No. 12/862,333, filed on Aug. 24, 2010, now abandoned.

(60) Provisional application No. 61/237,195, filed on Aug. 26, 2009, provisional application No. 61/237,287, filed on Aug. 26, 2009, provisional application No. 61/236,795, filed on Aug. 25, 2009, provisional application No. 61/236,293, filed on Aug. 24, 2009.

(51) Int. Cl.
*G01N 27/447* (2006.01)

(52) U.S. Cl.
CPC .... *G01N 27/44721* (2013.01); *G01N 27/44778* (2013.01)

(58) Field of Classification Search
CPC ........... G01N 27/447; C07K 1/26; C07K 1/28
USPC .......... 204/600–606, 450, 466, 467, 456, 457
See application file for complete search history.

(56) References Cited

U.S. PATENT DOCUMENTS

| 3,620,947 A | 11/1971 | Allen et al. |
| D231,609 S | 5/1974 | Broek et al. |

(Continued)

FOREIGN PATENT DOCUMENTS

| CA | 2381962 | 3/2001 |
| WO | 96/13717 | 5/1996 |

(Continued)

OTHER PUBLICATIONS

Bio-Rad, "Automating electrophoresis with the new Experion (TM) System", BioRadiations, vol. 115, Jan. 1, 2005, 2-3.

(Continued)

*Primary Examiner* — Jennifer Dieterle

(57) ABSTRACT

The present teachings provide methods, devices, systems, and materials for performing electrophoresis in an automated fashion. The electrophoresis system may simultaneously image gel during an electrophoresis run. In some embodiments, the electrophoresis system may analyze an imaged gel during or after electrophoresis. The device may comprise a gel processing system, a gel illumination system, an image capture system, and an image analysis all housed within a housing.

21 Claims, 15 Drawing Sheets

(56) References Cited

U.S. PATENT DOCUMENTS

| | | | |
|---|---|---|---|
| 4,164,464 A | 8/1979 | Allington et al. | |
| 4,294,684 A | 10/1981 | Sewer | |
| D282,352 S | 1/1986 | Hoefer et al. | |
| 4,608,146 A | 8/1986 | Penaluna | |
| 4,773,984 A | 9/1988 | Flesher et al. | |
| 4,795,541 A | 1/1989 | Hurd et al. | |
| 4,810,348 A | 3/1989 | Sarrine et al. | |
| 4,830,725 A | 5/1989 | Berninger et al. | |
| D303,007 S | 8/1989 | Flesher et al. | |
| 5,073,246 A | 12/1991 | Chu et al. | |
| 5,147,522 A | 9/1992 | Sarrine | |
| 5,284,565 A | 2/1994 | Chu et al. | |
| 5,318,682 A | 6/1994 | Singer | |
| 5,338,426 A | 8/1994 | Shigeura et al. | |
| 5,407,552 A | 4/1995 | Lebacq | |
| 5,411,657 A | 5/1995 | Leka | |
| 5,626,735 A | 5/1997 | Chu et al. | |
| 5,627,022 A | 5/1997 | Renfrew et al. | |
| 5,632,877 A | 5/1997 | Van Atta | |
| 5,656,145 A | 8/1997 | Nguyen et al. | |
| 5,685,967 A | 11/1997 | Manis et al. | |
| 5,717,602 A | 2/1998 | Kenning | |
| 5,785,835 A | 7/1998 | Saito et al. | |
| 5,799,773 A | 9/1998 | Heffelfinger et al. | |
| 5,800,691 A | 9/1998 | Kozulic | |
| 5,891,314 A | 4/1999 | Heffelfinger et al. | |
| 5,897,760 A | 4/1999 | Heffelfinger et al. | |
| 5,949,899 A | 9/1999 | Ng | |
| 5,951,838 A | 9/1999 | Heffelfinger et al. | |
| 5,993,628 A | 11/1999 | Selby et al. | |
| 6,063,250 A | 5/2000 | Becker et al. | |
| RE36,826 E * | 8/2000 | Fujimiya et al. | 204/461 |
| D430,304 S | 8/2000 | Oonuma et al. | |
| 6,139,709 A | 10/2000 | Scott | |
| 6,231,813 B1 | 5/2001 | Ally et al. | |
| D516,733 S | 3/2006 | Pedraza et al. | |
| D524,948 S | 7/2006 | Pedraza et al. | |
| D564,378 S | 3/2008 | Kaushal et al. | |
| D564,924 S | 3/2008 | Kaushal et al. | |
| D667,134 S | 9/2012 | Updyke et al. | |
| 2002/0079222 A1 | 6/2002 | Sevigny et al. | |
| 2003/0157720 A1 * | 8/2003 | Li | 436/15 |
| 2003/0168339 A1 * | 9/2003 | Audeh | 204/616 |
| 2003/0207271 A1 * | 11/2003 | Holwitt et al. | 435/6 |
| 2004/0033591 A1 | 2/2004 | Lubman et al. | |
| 2004/0036036 A1 * | 2/2004 | Atkinson et al. | 250/458.1 |
| 2005/0089930 A1 * | 4/2005 | Schneider et al. | 435/7.1 |
| 2005/0103633 A1 | 5/2005 | Tseng | |
| 2005/0213093 A1 | 9/2005 | Nordman et al. | |
| 2006/0032747 A1 | 2/2006 | Anderson et al. | |
| 2006/0176461 A1 | 8/2006 | Sekine | |
| 2006/0176481 A1 | 8/2006 | Forest et al. | |
| 2007/0045118 A1 * | 3/2007 | Maruo et al. | 204/606 |
| 2007/0102298 A1 | 5/2007 | Riveron Rojas et al. | |
| 2007/0278102 A1 * | 12/2007 | Hayashida et al. | 204/622 |
| 2007/0284250 A1 * | 12/2007 | Magnant et al. | 204/459 |
| 2008/0142365 A1 | 6/2008 | Kober et al. | |
| 2011/0042213 A1 | 2/2011 | Updyke et al. | |
| 2011/0042217 A1 | 2/2011 | Updyke et al. | |
| 2012/0247958 A1 | 10/2012 | Updyke et al. | |
| 2013/0175172 A1 | 7/2013 | Updyke et al. | |

FOREIGN PATENT DOCUMENTS

| | | |
|---|---|---|
| WO | 98/16820 | 4/1998 |
| WO | WO 98/25136 | 6/1998 |
| WO | 99/54721 | 10/1999 |
| WO | 01/16589 | 3/2001 |
| WO | WO 2011/025781 | 3/2011 |
| WO | WO 2011/028532 | 3/2011 |

OTHER PUBLICATIONS

EP10812553.5 Extended European Search Report, Jan. 22, 2013, pp. 1-10.

PCT/US2010/46506 International Search Report and Written Opinion Mailed on Oct. 15, 2010.

Phywe, "Electrophoresis chamber, Vertical. Product No. 35018-20", http://www.phywe.com/461/apg/360/pid/27438/Elektrophorese-Kammer,-vertikal-htm>., Feb. 13, 2013.

* cited by examiner

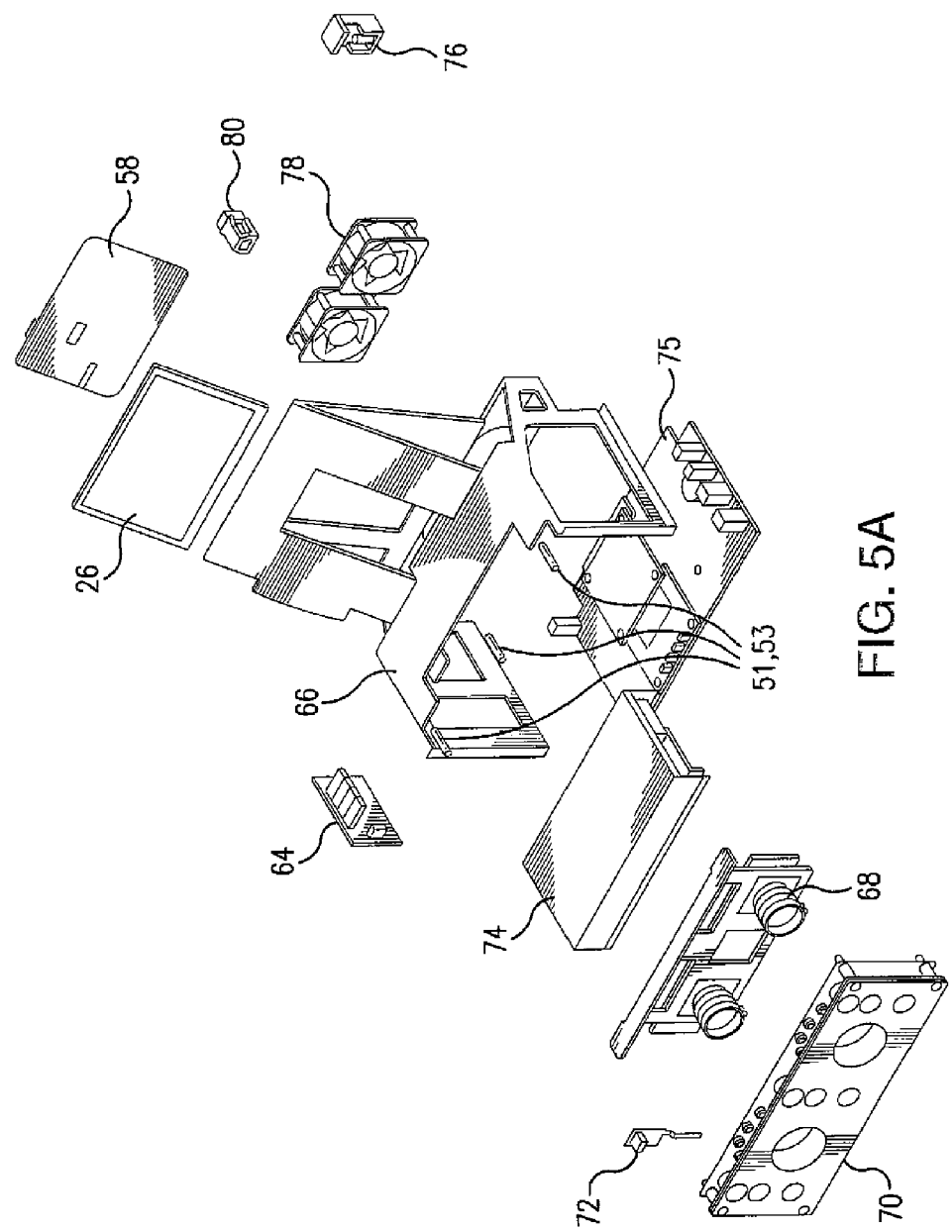

GEL ELECTROPHORESIS, IMAGING, AND ANALYSIS METHODS, DEVICES, SYSTEMS, AND MATERIALS

CROSS-REFERENCE TO RELATED APPLICATIONS

The present application is a continuation and claims the right of priority under 35 U.S.C. §120 to U.S. patent application Ser. No. 12/862,333, filed Aug. 26, 2009, now abandoned, which claims the benefit of U.S. Provisional Patent Applications Nos. 61/237,287 filed Aug. 26, 2009, 61/237,195 filed Aug. 26, 2009, 61/236,795 filed Aug. 25, 2009, and 61/236,293 filed Aug. 24, 2009, which are incorporated herein in their entireties by reference.

FIELD

The present disclosure generally relates to systems for performing electrophoresis. The disclosure further relates to electrophoresis systems capable of simultaneously imaging a gel during electrophoresis. The disclosure relates yet further to electrophoresis systems capable of analyzing an imaged gel during or after electrophoresis.

BACKGROUND

Gel electrophoresis is a common procedure for the separation of biological molecules, such as DNA, RNA, polypeptides and proteins. In gel electrophoresis, molecules can be separated into bands according to the rate at which an imposed electric field causes them to migrate through a filtering gel. A gel enclosed in a glass tube or sandwiched as a slab between glass or plastic plates can be utilized. Gels have an open molecular network structure, defining pores that are saturated with an electrically conductive buffered solution of a salt. These pores are large enough to enable passage of the migrating macromolecules through the gel.

Polyacrylamide gels are commonly used for electrophoresis. Other gels suitable for electrophoresis include agarose gels and starch gels. Polyacrylamide gel electrophoresis or PAGE is popular because the gels are optically transparent, electrically neutral and can be made with a range of pore sizes. Methods of making PAGE gels are well known. See, for example, B. Hames and D. Rickwood, *Gel Electrophoresis of Proteins* (2d ed. Oxford University Press, 1990); and A. Andrews, *Electrophoresis* (2nd ed. Oxford University Press, 1986). In general, stock solutions containing acrylamide monomer, a crosslinker such as bisacrylamide, gel buffers, and modifying agents such as sodium dodecyl sulphate ("SDS") are prepared. These stock solutions can be stored until a gel is needed. To manufacture a gel, the stock solutions are mixed with water in proportions according to the final desired concentrations of the various constituents. The gel is placed in a chamber in contact with buffer solutions which make electrical contact between the gel and the cathode or anode of an electrical power supply. A sample containing macromolecules and a tracking dye can be placed on top of the gel. An electric potential can be applied to the gel causing the sample macromolecules and tracking dye to migrate toward the bottom of the gel. The electrophoresis is halted just before the tracking dye reaches the end of the gel.

The locations of the bands of separated macromolecules are determined by staining the macromolecules in a sample staining apparatus and then imaging the gel in a separate imaging apparatus. Oftentimes, the image from the imaging apparatus must be manipulated in order to review the results and identify the positions of the various bands. By comparing the distance moved by particular bands in comparison to the tracking dye and macromolecules of known mobility, the mobility of other macromolecules can be determined. Thereby, the size of the macromolecules can then be calculated. Existing methods of electrophoresis require multiple time consuming steps and multiple pieces of large equipment to perform the electrophoresis, the gel staining, the imaging, and the image manipulation/analysis. A need exists in the art for better gel electrophoresis methods, devices, systems, and materials.

SUMMARY

The methods, devices, systems, and materials described herein address these needs by providing a gel electrophoresis device that performs at least one of the gel processing, image capture, and image analysis, resulting in, among other things, reduced time for conducting electrophoresis, reduced instrument cost, and reduced instrument footprint compared to existing instruments for and methods of electrophoresis.

According to various embodiments of the present teachings, a gel electrophoresis device is provided that may comprise at least one of a gel processing system, a gel illumination system, an image capture system, and an image analysis system. The present teachings also provide one or more system alone or in combination. In some embodiments, the gel processing device may include a gel processing system, a gel illumination system, an image capture system, and an image analysis system. In some embodiments, the gel processing device may include one or more gel buffer reservoirs, two or more gel buffer reservoirs, one or more gel holders, or two or more gel holders. In some embodiments, the gel processing device may include one or more imaging systems. In some embodiments, the gel processing device may include one or more image capture systems. In some embodiments, the gel processing device may include one or more image analysis systems. In some embodiments, the gel processing device may include one or more processors. In some embodiments, the gel processing device may include any other suitable components for processing and/or analyzing a gel, including but not limited to coupling, purification, isolation, or any other component for downstream processing of the gel.

According to various embodiments, a method of performing gel electrophoresis is provided that may comprise at least one of obtaining a gel electrophoresis system, obtaining at least one sample labeled with a fluorescent dye, performing electrophoresis on the at least one labeled sample, and imaging the at least one labeled sample. In some embodiments, the method of performing gel electrophoresis may include obtaining a gel electrophoresis system, obtaining at least one sample labeled with a fluorescent dye, performing electrophoresis on the at least one labeled sample, and imaging the at least one labeled sample. The method may further include analyzing the imaged sample, obtaining a hard copy of the analyzed image, and/or electrophoresing a labeled protein standard simultaneously with the labeled sample. In some embodiments, at least two proteins are included in the labeled protein standard and are labeled with the same fluorescent dye as the labeled sample. In some embodiments, the method may further include determining the molecular weight of the labeled sample, determining the relative amount of at least one labeled protein in the sample, and/or determining the absolute amount of at least one labeled protein in the sample.

BRIEF DESCRIPTION OF THE DRAWINGS

A better understanding of the features and advantages of the present disclosure will be obtained by reference to the accompanying drawings, which are intended to illustrate, not limit, the present teachings.

FIG. 5A is an exploded perspective view of the electronic assembly of the gel electrophoresis device shown in FIG. 1.

DETAILED DESCRIPTION OF THE DISCLOSURE

Figure 1:
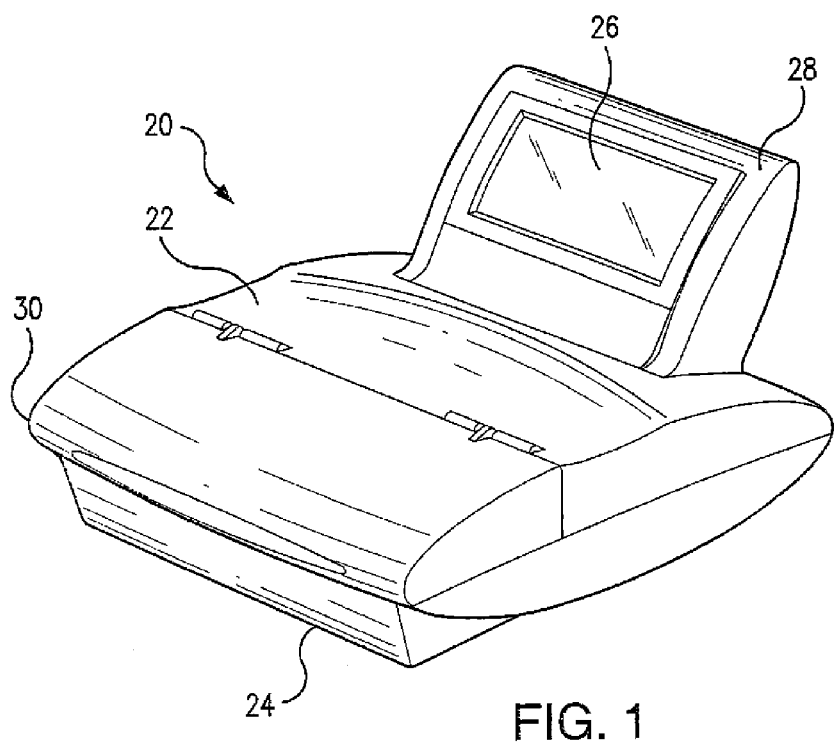
FIG. 1 is a schematic representation of a gel electrophoresis device in accordance with an embodiment of the present teachings.

According to various embodiments, the present teachings provide a gel electrophoresis device, an embodiment of which is shown by reference numeral 20 in FIG. 1. Gel electrophoresis device 20 comprises a housing 22, a base 24, an LCD display 26, a user interface 28, and a housing lid 30. LCD display 26 may be operably associated with user interface 28.

Figure 2A:
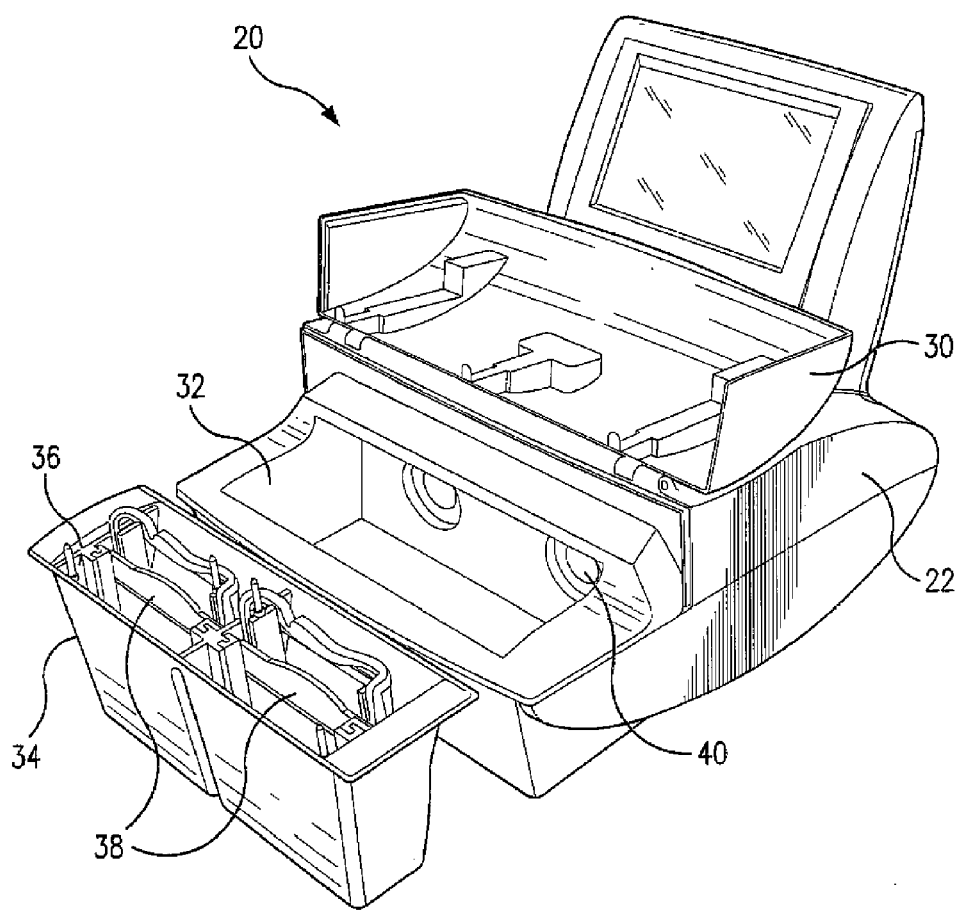
FIG. 2A is a perspective view of the gel electrophoresis device shown in FIG. 1 with the housing lid open and showing the gel running tanks removed from the system.
Figure 2B:
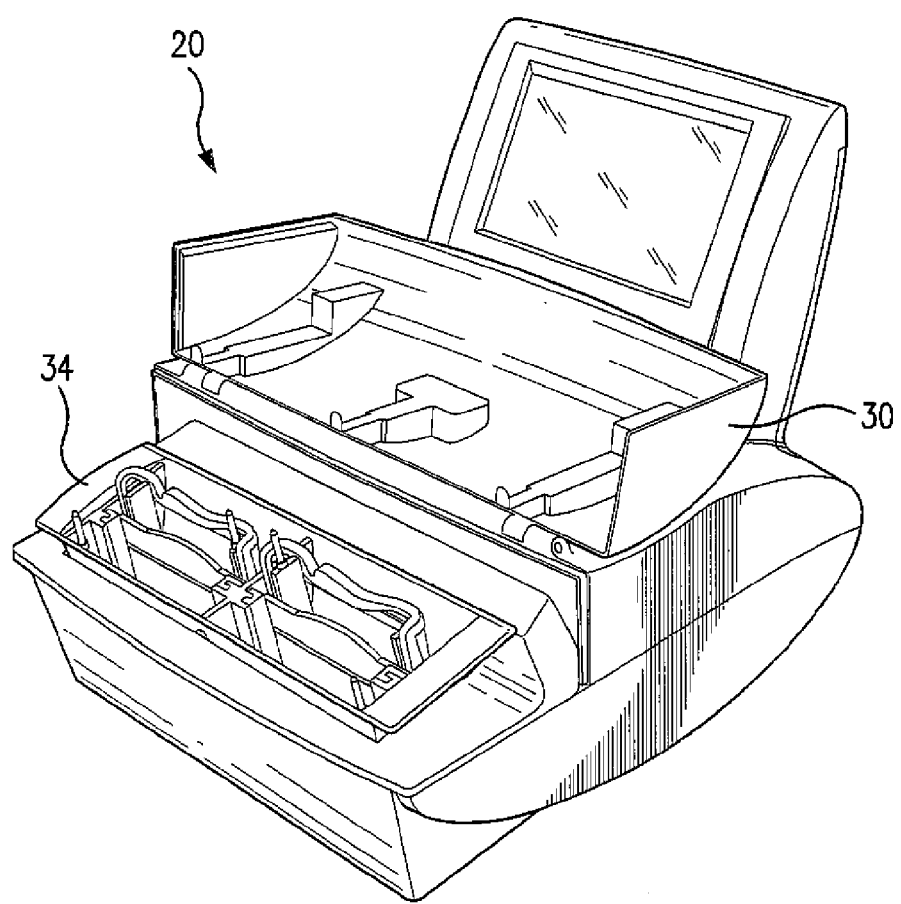
FIG. 2B is a perspective view of the gel electrophoresis device shown in FIG. 2A, wherein the housing lid is open and the gel running tanks are positioned in the gel running chamber.

A perspective view of gel electrophoresis device 20 in an open configuration is shown in FIG. 2A. As can be seen, a gel tank chamber 32 may be provided within housing 22 of gel electrophoresis device 20. Gel tank chamber 32 may provide an interior compartment for a gel running tank 34. As shown in FIG. 2A, gel running tank 34 is removed from or in a disengaged position from the gel running chamber 32 of housing 22. Within gel running tank 34 may be at least one buffer reservoir 36 and operably associated with buffer reservoir 36 may be at least one gel cassette 38. As shown in FIG. 2A, gel running tank 34 may include a buffer reservoir 36 divided in two portions; however, in some embodiments, one or more portions may be provided rather than two in particular. Similarly, as shown in FIG. 2A, two gel cassettes 38 are shown operably associated with buffer reservoir 36, but for various embodiments one or more gel cassettes 38 may be provided. Also shown in FIG. 2A is a gel imaging system 40, which may be operably associated with gel tank chamber 34. FIG. 2B shows the gel electrophoresis device 20 of FIG. 2B in a perspective view and in an open configuration in which gel running tank 34 is inserted into and operably associated with gel tank chamber 32. In both FIGS. 2A and 2B, housing lid 30 is in an open configuration in respect to housing 22.

Figure 3A:
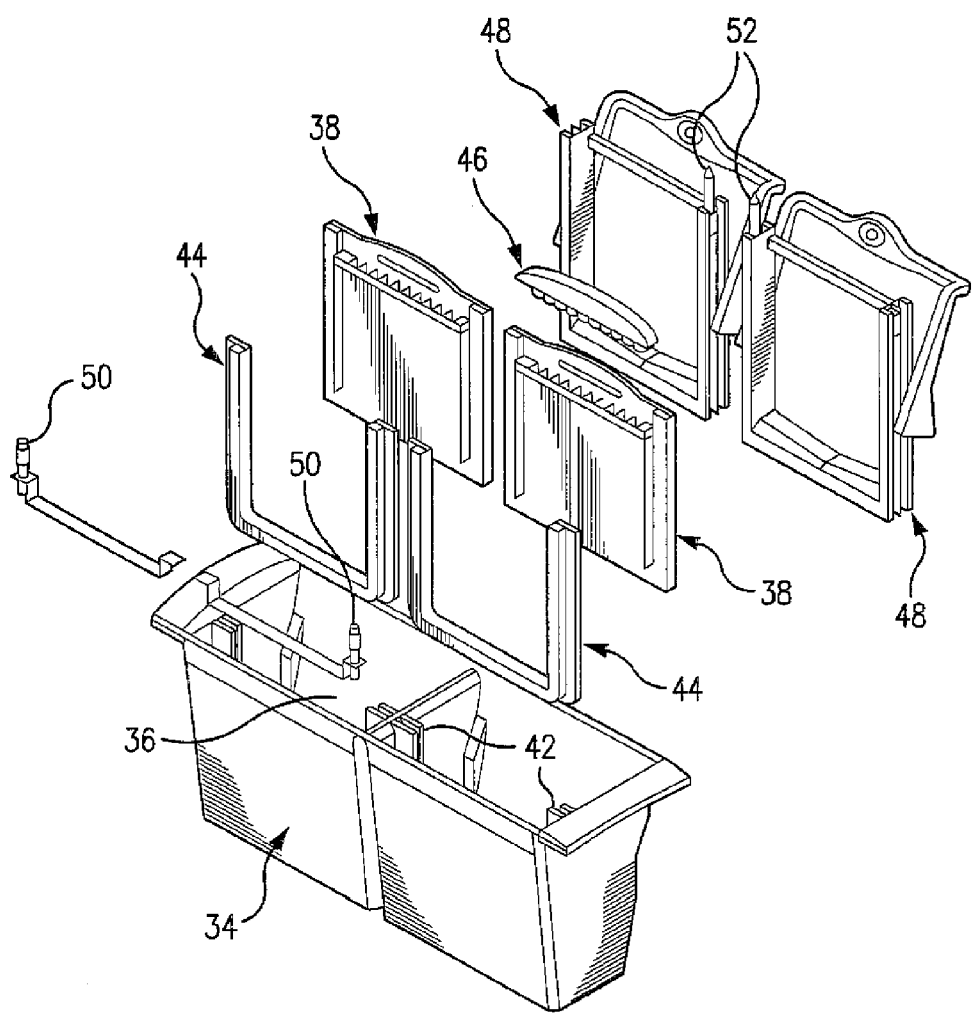
FIG. 3A is a schematic representation of an exploded perspective view of a gel running assembly in accordance with an embodiment of the present teachings.

FIG. 3A is a schematic representation of an exploded perspective view of gel electrophoresis device 20. Gel cassettes 38, two of which are shown for demonstrative purposes, may be provided as well as respective wedge well combs 46 capable of operatively associating with the gel cassettes. A gel holder 42 may be operably associated with buffer reservoir 36, allowing insertion of gel cassettes 38. At least one first electrode 50 may be capable of being operatively associated with buffer reservoir 36. At least one second electrode 52 may be capable of being operably associated with clamps 48. Rubber gaskets 44 are also shown and are capable of being operatively associated with the buffer reservoir 36 and gel cassettes 38.

Figure 3B:
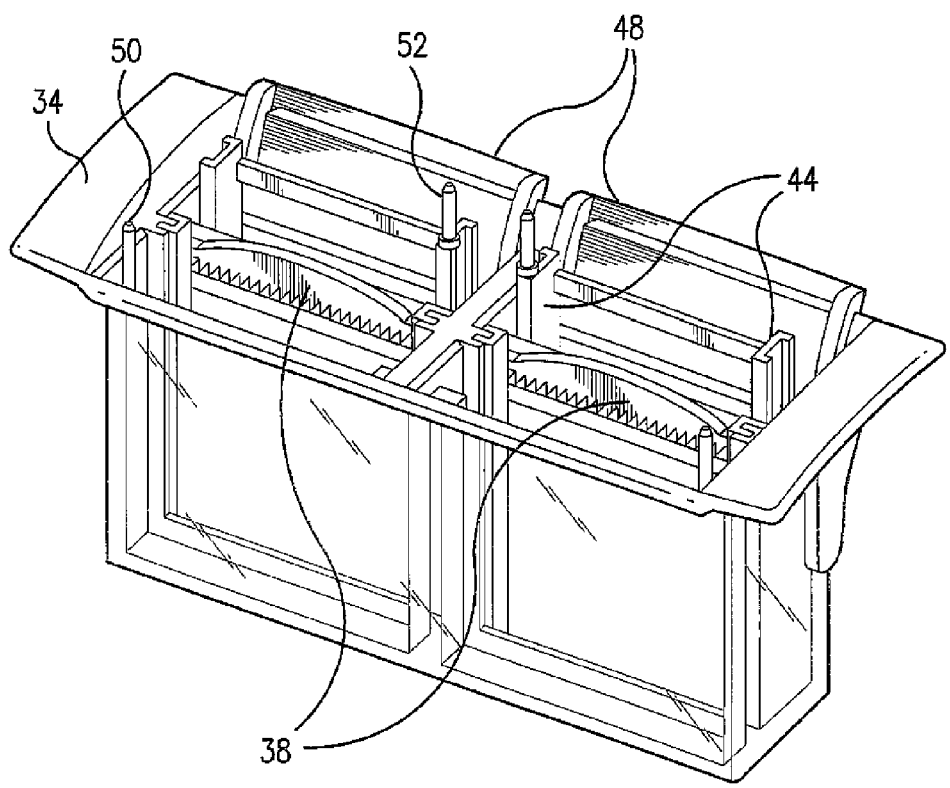
FIG. 3B is a perspective view of the gel running assembly shown in FIG. 3A in an assembled state.

FIG. 3B is a perspective view of gel running tank 34 shown disengaged from gel tank chamber 32 of electrophoresis device 20 and including the buffer reservoir 36, with gel cassettes 38 inserted into buffer reservoirs 36. In some embodiments, also inserted into and operatively associated with buffer reservoir 36 may be rubber gaskets 44, clamps 48, and electrodes 52. Electrodes 50 are also shown as operably associated with gel running tank 34 and reservoir 36. Electrodes 50 and 52 can together form electrode pairs across which an electrokinetic field may be established.

Figure 4:
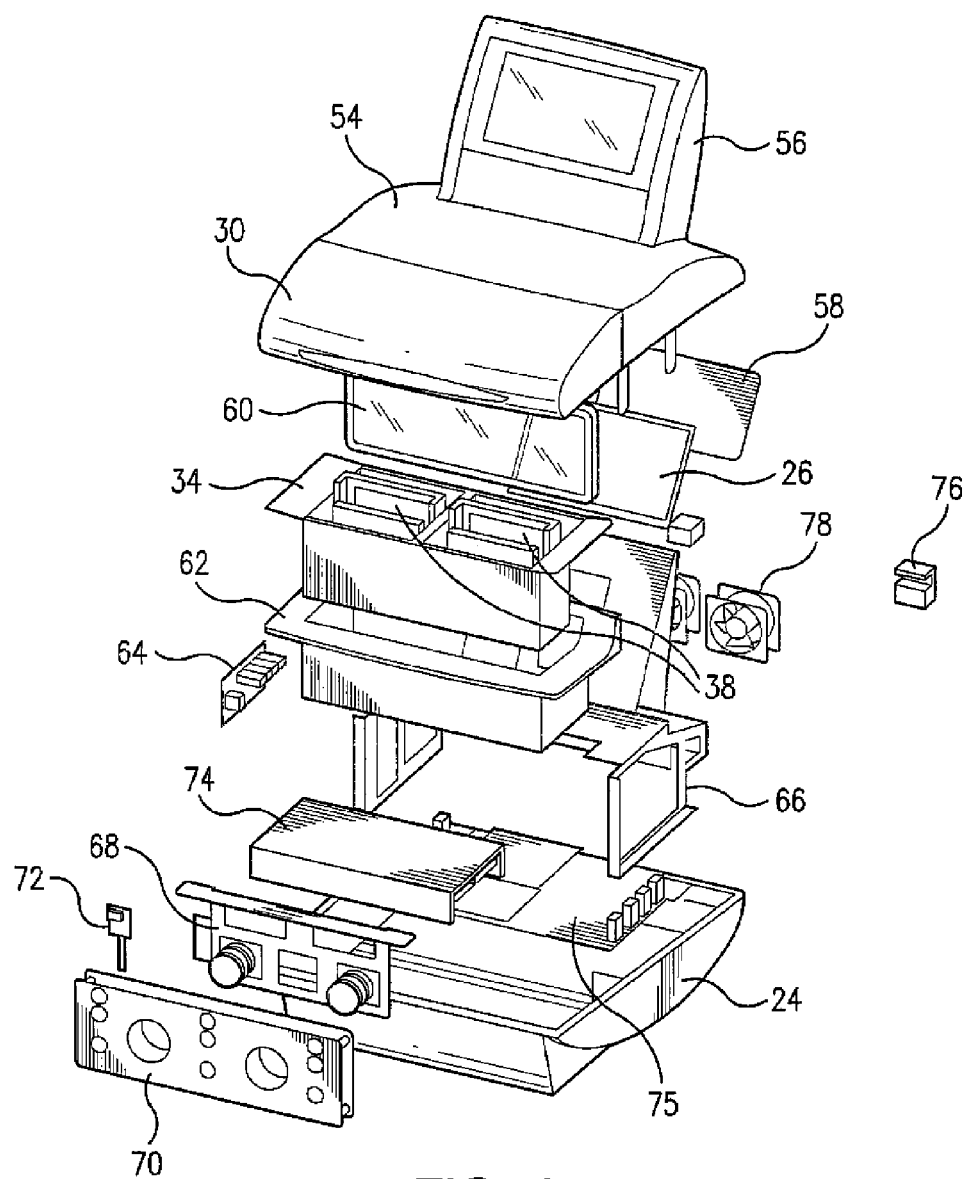
FIG. 4 is an exploded perspective view of the gel electrophoresis device shown in FIG. 1.

FIG. 4 is an exploded perspective view of gel electrophoresis device 20. The following components are collectively operably associated together and form parts of gel electrophoresis device 20. Upper housing 54 is operably associated with housing 22 and forms parts of the same. Housing lid 30 is operably associated with upper housing 54, for example, through one or more hinges. A display cover 56 can include a forward-facing portion constituting user interface 28 (FIG. 1). Display cover 56 is shown operably associated with upper housing 54 and at least partially rests above display 26. Operably associated with the display 26 is processor 58. A protective window 60 is operably associated with the gel tank chamber 32. Within gel tank chamber 42, is gel running tank 34 and buffer reservoir 36. Gel cassettes 38 are inserted and operably associated with buffer reservoir 36. A running tank seal 62 is operably associated with and forms part of gel tank chamber 32. In some embodiments, a low level controller 64 may be present. A chassis 66 is operably associated with the gel tank chamber 32, as well as other compartments of electrophoresis device 20. A camera assembly 68 is provided and is operably associated with gel tank chamber 32. A light emitting diode (LED) assembly 70 is provided operably associated with camera assembly 68. A safety switch 72 is operably associated with LED assembly 70. A first power supply 74 is provided and a second power supply 75 may also be provided. In some embodiments the first power supply 74 may comprise a low voltage power supply, second power supply 75 comprises a high voltage power supply, or vice versa. Power supplies 74 and 75 may be integrated to form a continuous power device. An off-on switch 76 may be operably associated with at least one of first power supply 74 and second power supply 75. A fan 78 may be operably associated with housing 22.

FIG. 5A is an exploded perspective view of gel electrophoresis device 20 with housing 22 removed. Shown in FIG.

Figure 5B:
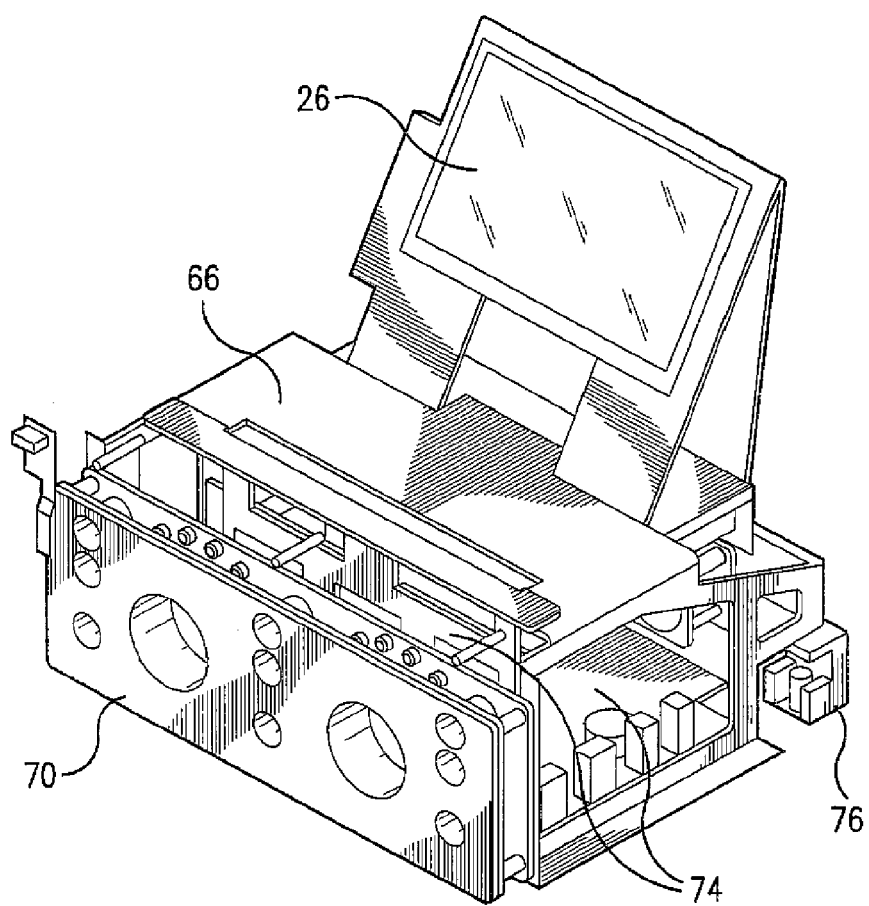
FIG. 5B is a perspective view of the electronic assembly shown in FIG. 5A, in an assembled state.

5A are the following components that are collectively operably associated with each other and with and within gel electrophoresis device 20. Processor 58, touch screen display 26, chassis 66, low level controller 64, first power supply 74, second power supply 75, electrode connectors 51 and 53, camera assembly 68, safety switch 72, LED assembly 70, as well as on-off switch 76, fan 78, and Ethernet port 80. Corresponding to FIG. 5A, FIG. 5B is a perspective view of assembled gel electrophoresis device 20 with housing 22 removed. Shown in FIG. 5B are the following components which are collectively operably associated touch screen display 26, chassis 66, LED assembly 70, power supply 74, and on-off switch 76.

Figure 6A:
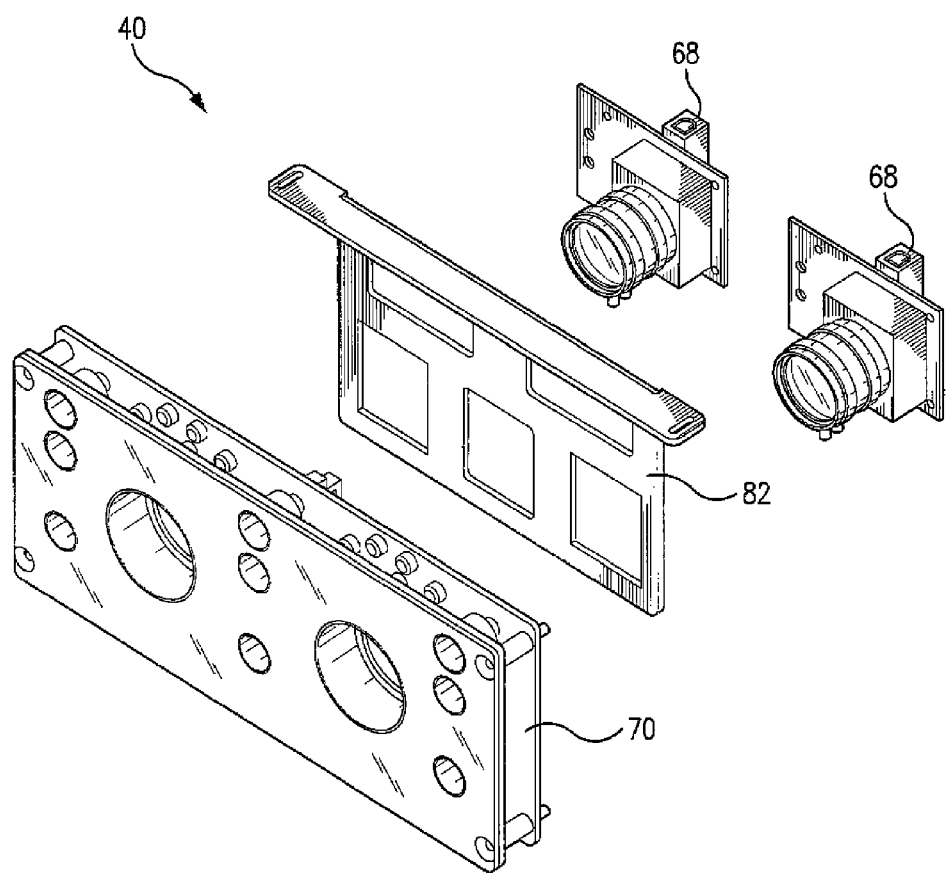
FIG. 6A is an exploded perspective view of the imaging system of the electrophoresis device shown in FIG. 1, including the camera assembly and the light emitting diode (LED) assembly.
Figure 6B:
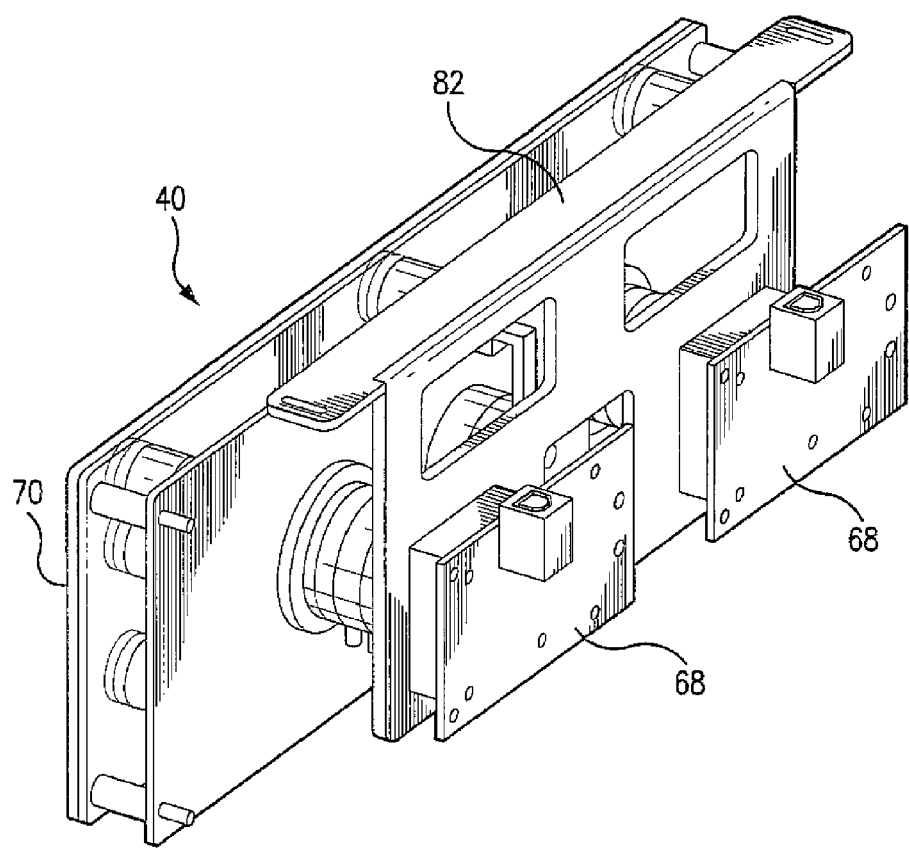
FIG. 6B is a backside perspective view of the imaging system shown in FIG. 6A, in an assembled state.

FIG. 6A is an exploded perspective view of gel imaging system 40, including camera assembly 68, camera holder 82, and LED assembly 70. FIG. 6B is a perspective view of gel imaging system 68 in an assembled configuration corresponding to the exploded view shown in FIG. 6A. LED assembly 70, camera 68, and camera holder 82 are shown in operable association.

Figure 7A:
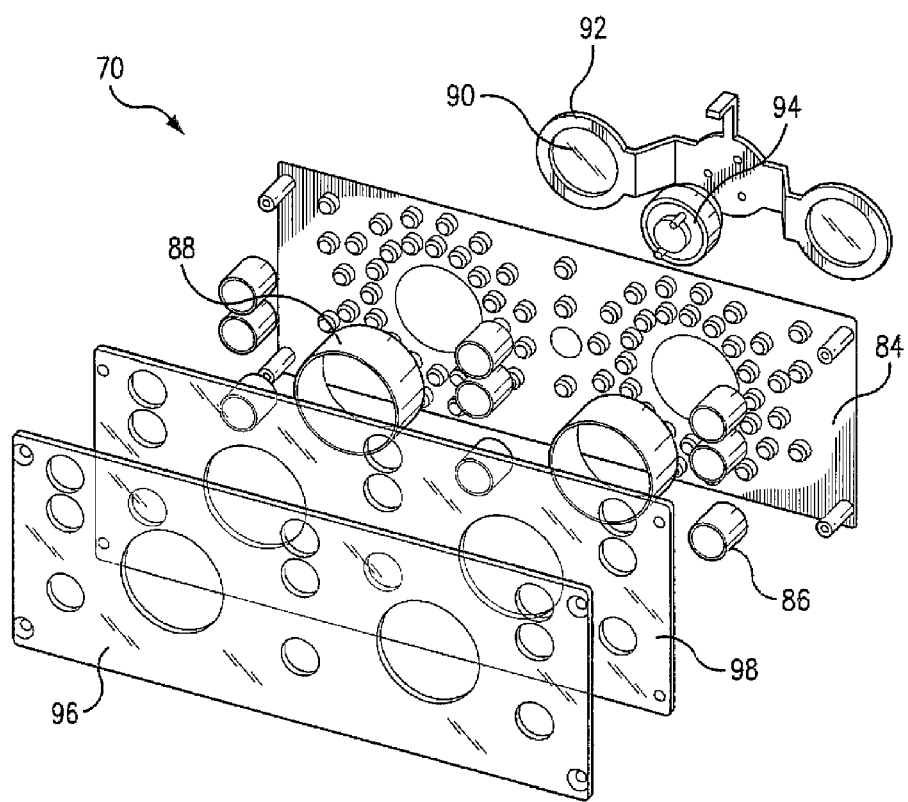
FIG. 7A is an exploded perspective view of the LED assembly of the gel electrophoresis device shown in FIG. 1.
Figure 7B:
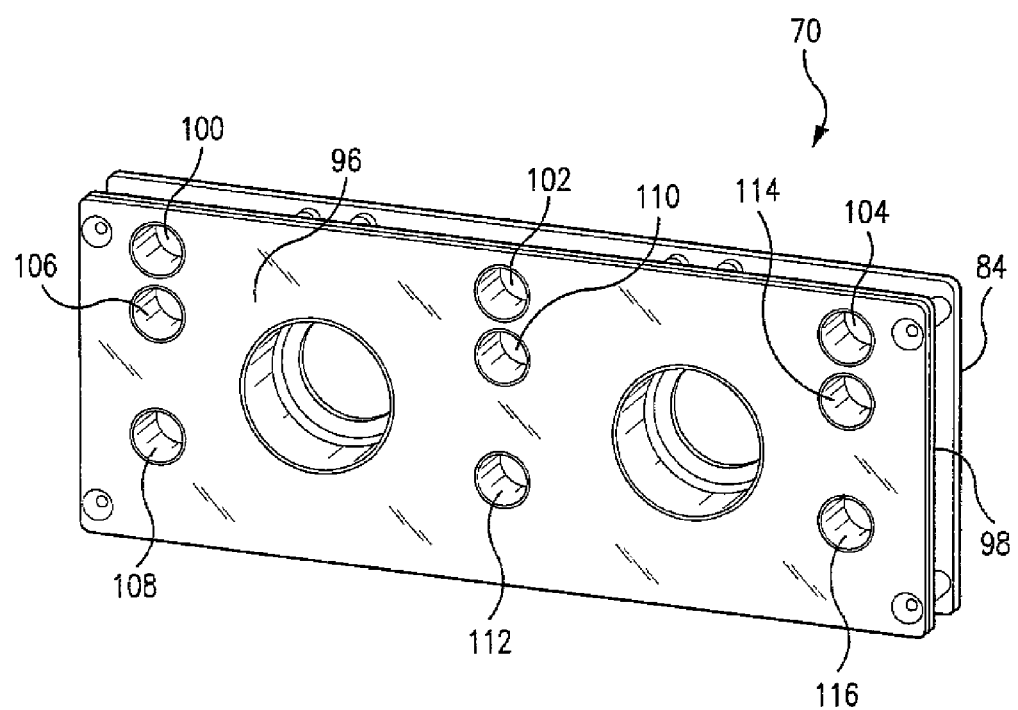
FIG. 7B is a front perspective view of the LED assembly shown in FIG. 7A, in an assembled state.
Figure 7C:
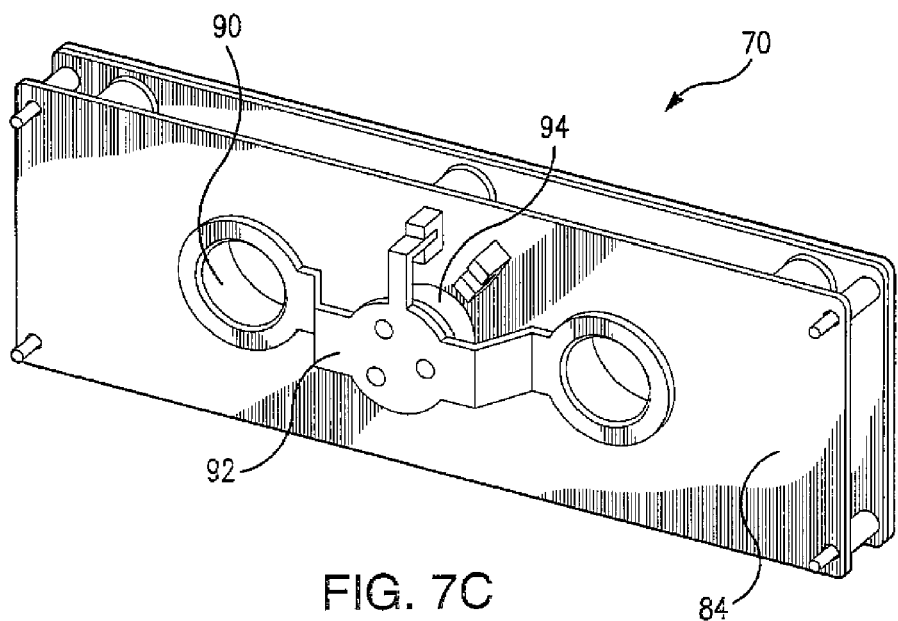
FIG. 7C is a rear perspective view of the LED assembly shown in FIGS. 7A and 7B, in an assembled state.

FIG. 7A is an exploded perspective view of LED assembly 70. Shown are LED printed circuit board (PCB) assembly 84, membrane light protective tube 86, of which there may be one or more, and camera protective tube 88, of which there may be one or more present. A primary filter 90 is shown operably associated with filter bracket 92, which in turn is operably associated with filter solenoid 94. Also shown is a secondary filter 96 and diffuser 98. FIG. 7B shows a first perspective view of one side of LED assembly 70. A secondary filter 96 is shown as are sample well lights 100, 102, and 104. The number of sample well lights can be one or more. Lights 106, 108, 110, 111, 112, 114, and 116 are shown, but the number of membrane lights can be one or more. The number of sample well lights and membrane lights may be varied as appropriate for a particular embodiment. LED PCB assembly 84, diffuser 98, and a secondary filter 96 are also shown. FIG. 7C shows a second perspective view of LED assembly 70, from a side opposite that shown in FIG. 7B. Depicted in FIG. 7C, and operably associated with one another, are the following components—primary filter 90, filter bracket 92, filter solenoid 94, and LED PCB assembly 84.

Figure 8A:
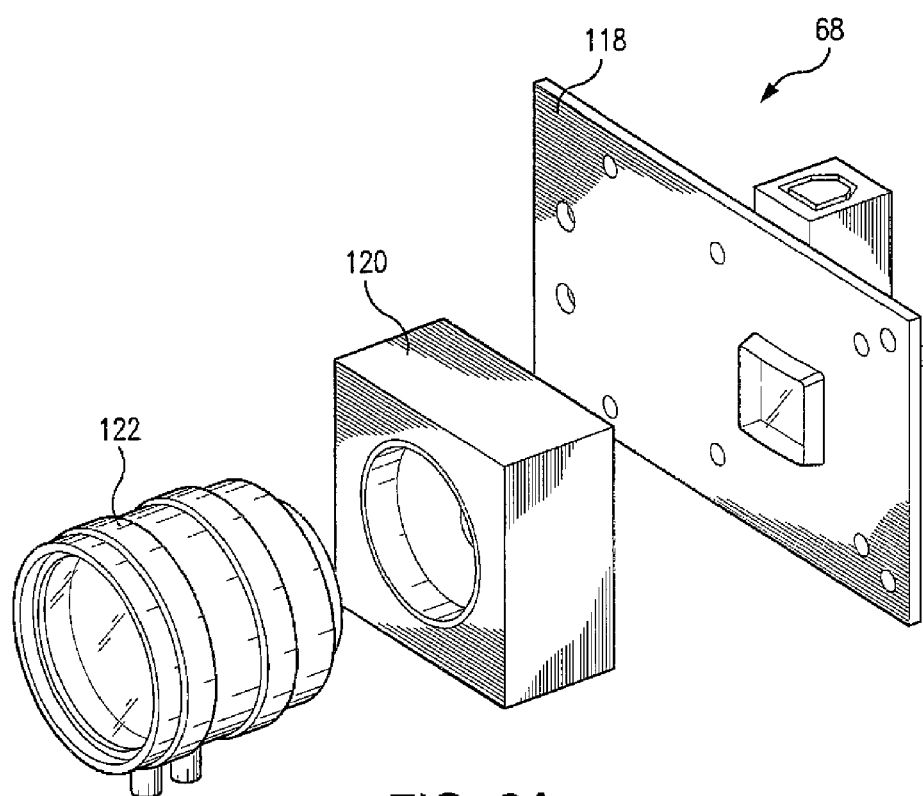
FIG. 8A is an exploded perspective view of the camera assembly of the gel electrophoresis device shown in FIG. 1.
Figure 8B:
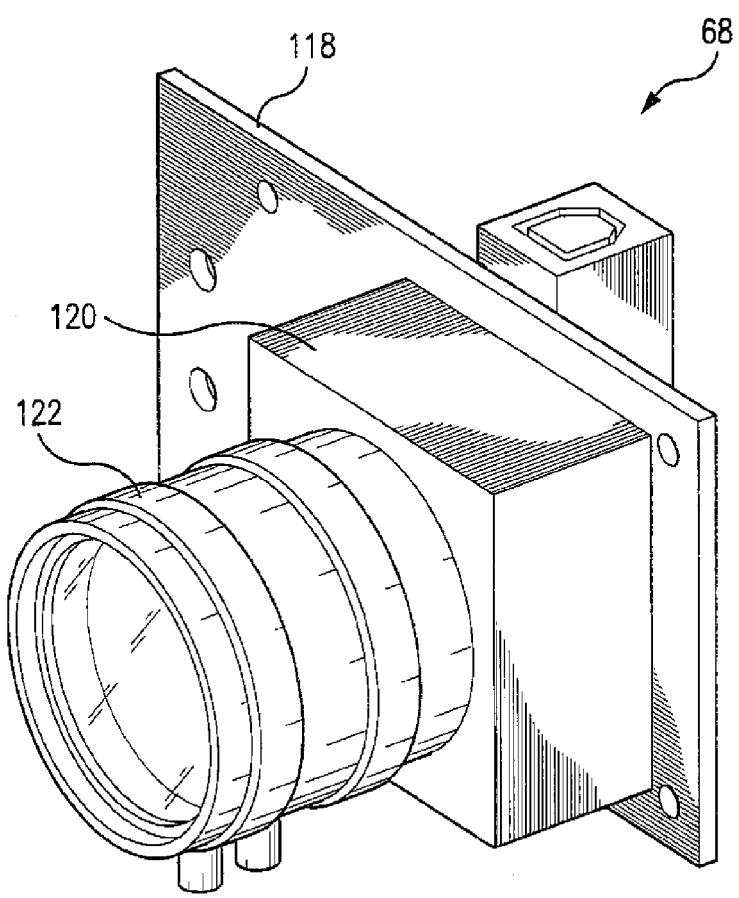
FIG. 8B is a front perspective view of the camera assembly shown in FIG. 8A, in an assembled state.

FIG. 8A shows an exploded perspective view of camera assembly 68. FIG. 8A shows camera PCB 118, lens holder 120, and lens assembly 122. FIG. 8B is an assembled perspective view of camera assembly 68 corresponding to that shown in FIG. 8A.

In accordance with various aspects of the present disclosure, a gel electrophoresis device is provided that can comprise a gel processing system, a gel illumination system, an image capture system, and an image analysis system; wherein the systems can be operably associated and automated. In some embodiments, the gel processing system comprises at least one gel buffer reservoir. In some embodiments, the gel processing system comprises at least two gel buffer reservoirs. In some embodiments, the at least one gel buffer reservoir comprises at least one gel holder. In some embodiments, the at least one gel buffer reservoir comprises at least two gel holders. In some embodiments, the gel processing system comprises at least one anode and at least one cathode. In some embodiments, the gel processing system comprises at least one anode and at least one cathode for each of the at least one gel holders. In some embodiments, the gel processing system may also comprise at least one power supply.

In some embodiments, the gel illumination system may comprise at least one light source. The at least one light source may be configured to illuminate at least one electrophoresis gel when the gel is placed in the gel processing system. In some embodiments, the at least one light source may comprise at least one blue light source. In some embodiments, the at least one light source, emits light in a wavelength range of from about 400 nm to about 800 nm. For example, in some embodiments, the at least one light source may emit light in a wavelength range corresponding to blue light (~475 nm). In some embodiments, the at least one light source emits light in a wavelength range of from about 500 nm to about 700 nm. In some embodiments, the at least one light source emits light in a wavelength range of from about 520 nm to about 640 nm. In some embodiments, the at least one light source comprises at least one LED such as, for example purposes only, at least one LED blue light source. In some embodiments, the at least one LED light source comprises multiple LEDs such as, for example purposes only, a blue light source comprising multiple LEDs. In some embodiments, an LED driver may be provided. Any appropriate type of LED may be used. In some embodiments, a Cree XREBLU series LED is used, available from Cree Incorporated, of Durham, N.C. In some embodiments, at least 2, at least 4, at least 8, at least 16, at least 32, at least 40, at least 64 LEDs are used with or without a diffuser.

In some embodiments, the at least one light source may comprise at least two light sources. The gel illumination system may comprise at least one light source for each electrophoresis gel placed in the device. In some embodiments, the gel illumination system may further comprise at least one light-focusing device or at least one light manipulating device. The at least one light focusing device or at least one light manipulating device may be selected from the group consisting of lenses, mirrors, filters, wave plates, a combination thereof, and the like, or any other suitable light manipulating device. In some embodiments, the at least one light focusing device or at least one light manipulating device may comprise at least one light intensity controlling component. The at least one light intensity controlling component may be configured to control the intensity of the light illuminating a position at which an electrophoresis gel is placed into the device when the device is being used for electrophoresis. In some embodiments, the at least one light source may be pre-configured such that no additional manipulation of the gel illumination system is required, beyond automatic or manual activation of the system. The light source may be configured to provide sufficient illumination for successful image capture at the position at which an electrophoresis gel is placed into the device when the device is being used for electrophoresis.

In some embodiments, the image capture system may comprise at least one digital camera. The camera may comprise a complementary metal-oxide-semiconductor (CMOS) device. In some embodiments, the at least one digital camera may comprise at least 1.2 megapixels. In some embodiments, the image capture system may comprise at least one digital camera for each electrophoresis gel placed in the device. In some embodiments, the at least one digital camera may be configured to capture images at the position at which at least one electrophoresis gel is placed in the device when the device is being used for electrophoresis. In some embodiments, the at least one digital camera may be pre-configured such that no additional manipulation of the image capture system is required, beyond automatic or manual activation of the system, to provide successful image capture at the position at which an electrophoresis gel is placed into the device when the device is being used for electrophoresis. In some embodiments, the image capture system may be configured to provide real time imaging of at least one electrophoresis gel during electrophoresis.

In accordance with another aspect of the present teachings, a method of performing gel electrophoresis is provided. The method can comprise the steps of obtaining a gel electrophoresis device, obtaining at least one sample labeled with a fluorescent dye, performing electrophoresis on the at least one labeled sample, and imaging the at least one labeled sample. The performing and imaging steps may be operably associated with each other and automated. In some embodiments, the electrophoresis device is automated. The method may further comprise analyzing the imaged sample. The method may further comprise obtaining a hard copy of the analyzed image, for example, a printout. In some embodiments, the method may further comprise electrophoresing a labeled protein standard simultaneously with a labeled sample. In some embodiments, at least two labeled protein standards may be used and may be labeled with the same fluorescent dye as used to label the sample. The method may further comprise determining the molecular weight of the labeled sample. In some embodiments, the method may further comprise determining the relative amount of at least one labeled protein in the sample. In some embodiments, the method may further comprise determining the absolute amount of at least one labeled protein in the sample.

In some embodiments, an electrophoresis method may be performed in less than about 30 minutes. In some embodiments, the method may be performed in less than about 20 minutes. In some embodiments, the method is performed in less than about 15 minutes. The imaging may comprise exposing the labeled sample to at least one light source. In some embodiments, the imaging may comprise exposing the labeled sample to at least one blue light source. In some embodiments, the at least one blue light source may comprise an LED blue light source. In some embodiments, the at least one light source emits light in a wavelength range of from about 400 nm to about 800 nm, such as for example ~475 nm which corresponds to blue light. In some embodiments, the at least one light source emits blue light in a wavelength range of from about 520 nm to about 640 nm.

The gel electrophoresis device of the present teachings may comprise an integrated gel-based cassette instrument and an analysis system for protein analysis. The device may carry out a workflow for gel electrophoresis, providing a limited processing step process that encompasses introduction of one or more samples to an electrophoresis gel through generation of a results report. In some embodiments, the device may be automated.

In some embodiments, the electrophoresis device may provide for the processing of an electrophoresis gel from the point of introduction of one or more samples to an electrophoresis gel through generation of a report of results. In some embodiments, the processing may be accomplished in less than 60 minutes, less than 55 minutes, less than 50 minutes, or less than 45 minutes.

In some embodiments, the device may provide for real-time imaging of electrophoresis gels in the device during an electrophoresis run. In some embodiments, the real-time imaging may include real-time illumination and image capture of electrophoresis gels in the device during an electrophoresis run. The imaging may include activation and imaging of either or both of visible and/or fluorescent bands and band migration during an electrophoresis run.

In some embodiments, the gel electrophoresis device may be configured to run one or more gels at the same time, such as multiple gels at the same time, for example, from two to six gels, such as 2, 3, 4, 5, or 6 gels at the same time.

In some embodiments, the gel electrophoresis device may comprise an integrated instrument that may run, image, and analyze one or more gels at the same time. In some embodiments, the device may be integrated or fully integrated in that it may not require an external power supply, a separate computer or a central processing unit for control of the device, control of gel processing such as control of the electrophoresis process (including but not limited to one or more of voltage, current, and/or time used for the electrophoresis process), control of gel illumination, control of image capture, control of image processing, and/or control of post-electrophoresis analysis using an onboard user interface. The control of analysis may comprise, but may not be limited to, control of image analysis and/or control of report generation and display. In some embodiments, the gel processing device may include any other suitable components for processing and/or analyzing a gel, including but not limited to coupling, purification, isolation, or any other component for downstream processing of the gel.

In some embodiments, the gel electrophoresis device may be integrated or fully integrated in that it may include at least two of: a gel processing system, a gel illumination system, an image capture system, an analysis and control system, a power supply, a display, a computer, and/or a central processing unit. In some embodiments, the device may include a data transfer system such as a read-write CD ROM Drive or DVD drive, at least one USB port, and/or at least one Ethernet port. In some embodiments, the device may include pre-loaded software and/or Application Specific Integrated Circuits (ASICS) that may enable the control of the device, control of the image capture, control of the processing and analysis, and/or control of displaying and/or exporting the results. In some embodiments, the analysis may include one or more of molecular weight estimation for each of the individual bands, band percentage (% purity), and relative or absolute quantification of at least one analyte from one or more gel images captured by the device.

In some embodiments, the device may be configured to image a blot membrane and link it to the gel run data stored within the device. In such embodiments, the device may additionally include a white light source, an EPI fluorescence source, and a holder for a blot membrane. In some embodiments, the device may calculate the molecular weight estimation for each of the individual bands, calculate lane identity, and calculate relative or absolute quantification of at least one analyte based from the blot membrane.

In some embodiments, the device may be used with electrophoresis gel and buffer systems and methods as described, for example, in U.S. Provisional Patent Application 61/236, 293, filed Aug. 24, 2009, the contents of which are hereby incorporated by reference in their entirety. In some embodiments, the device can be used in accordance with the methods and standards and stains described in U.S. Provisional Patent Application No. 61/236,795, filed Aug. 25, 2009, the contents of which are hereby incorporated by reference in their entirety. In some embodiments, the device can be used with gel cassettes and combs configured as described in a U.S. Provisional Patent Application No. 61/237,195, filed Aug. 26, 2009, the contents of which are hereby incorporated by reference in their entirety.

In some embodiments, the device provides for a user to directly observe sample loading in wells of an electrophoresis gel when the gel is in the instrument. The device may be configured to fit on a laboratory bench top. In some embodiments, the device has a weight that is less than 35 kg, a height that is less than 55 mm, a width that is less than 60 mm and a depth that is less than 70 mm. In some embodiments, the device may include dye front tracking for molecular weight (MW) calculation and in some embodiments can include dye front tracking as an automatic run-stop option. In some embodiments, the device may provide an automatic run-stop based on a fixed time, such as a user selected time or a pre-loaded protocol time. The timing system may include a user override capability to stop early or to extend a run.

In some embodiments, the gel processing system may be configured to process one or more electrophoresis gel cassettes, such as from 1 to 6 gel cassettes, from 1 to 4 gel cassettes, from 1 to 3 gel cassettes, from 1 to 2 gel cassettes, or a single gel cassette. In some embodiments, the gel processing system and the device may be configured to process more than one gel cassette simultaneously. In some embodiments, the gel processing system and the device may be configured to process at least two gel cassettes simultaneously. In some embodiments, the gel processing system may be configured to independently (whether simultaneously or serially) process two or more gel cassettes. In some embodiments, the gel processing system may include at least one running tank, for example, from 1 to 6 running tanks, for example, from 1 to 4 running tanks, from 1 to 3 running tanks, from 1 to 2 running tanks, or a single running tank. In some embodiments, a running tank may be partitioned into multiple separate running reservoirs, such that multiple gel cassettes may be run at the same time in a single running tank without cross contamination between the running reservoirs. In some embodiments, each gel cassette may have a separate running tank. The running tank and/or running reservoirs may include a fill level indicator and/or a liquid level controller. In some embodiments, the device may be configured to provide for active temperature control of the buffer tank. In other embodiments, the device may be configured for passive temperature control of the running tank.

The running tank may include a gel holder for each gel cassette that may hold the gel cassette in a vertical orientation during processing and may help to seal the gel cassette in the running tank. In some embodiments, the gel holder may be movable such that a user may adjust the vertical positioning of a gel cassette within the gel holder. In some embodiments, the gel holder may be configured to act in conjunction with a gel cassette assembly and may comprise at least one sealing gasket, a seal and lock frame, and a cam lock handle to seal the gel cassette in the running tank.

In some embodiments, the seal and lock frame may be configured to receive a gel cassette. The seal and lock frame may receive the gel cassette via interaction between protrusions or slots on the gel cassette with slots or protrusions on the seal and lock frame. In some embodiments, the seal and lock frame may also include anode and/or cathode contacts and anode and/or cathode wires that may be sealed from the rest of the running reservoir via a sealing gasket. Each of the contacts and/or wires can independently comprise any suitable conducting substance, for example, a metal, copper, platinum, palladium, gold, alloys thereof, and the like, or any other suitable conductive material. In some embodiments, the cam lock handle may be included with the seal and lock frame and may be used to exert pressure against the seal and lock frame to ensure proper sealing of a gel cassette within the running tank. The seal and lock frame may be configured such that real-time image capture using other systems within the device is not interfered with by the seal and lock frame.

In use, a gel cassette may be loaded into a seal and lock frame and a sealing mechanism, such as a sealing gasket, may be placed along at least one edge of the seal and lock frame to form a gel cassette assembly. The gel cassette assembly may be placed into a gel holder in a running reservoir of a running tank and a cam lock handle may be engaged to lock and seal the assembly in place. The cam lock handle may also be used to help place the cassette into the holder or for removal after processing. The relevant buffers may be added into the running reservoir and the gel may be electrophoresed and further processed using the other device components. In some embodiments, the gel processing system is pre-configured such that no additional manipulation of the gel illumination system and/or the image capturing system and/or the image analysis system is required, beyond automatic or manual activation of the system. After an electrophoresis gel is placed into the device, the device may be used for electrophoresis and may provide suitable gel processing, image capture, and image analysis.

In some embodiments, the gel processing system may be connected to at least one internal power supply, which may provide the power supply needs used to electrophorese the gel cassettes for which the device is configured. In some embodiments, multiple power supplies may be used depending on the number of gel cassettes for which the device is configured to process. In some embodiments, the gel processing system may include contacts that may be connected to the relevant power supply via contacts in a lid that fits over the running tank. In this manner, the gel processing system may be isolated from the electrical system of the rest of the device, while the lid is open, and when the lid is closed the electrical contacts in the lid may interact with the anode and cathode contacts of the gel processing system to provide the electrokinetic fields appropriate for electrophoresis. In some embodiments, the arrangement of the various contacts on the lid and the gel assembly may prevent running an electrophoresis when the assembly and/or the gel cassette is installed backwards.

In some embodiments, the gel electrophoresis device may include a gel illumination system. Any suitable illumination system may be used. In some embodiments, the gel illumination system may include at least one light source. The light source may emit white light, or may emit any suitable wavelength of light, for example, light of a wavelength useful to excite light sensitive molecules that can be in the sample and/or are included with standards that are being processed in a gel cassette of the device. In some embodiments, the at least one light source may be configured to illuminate at least one electrophoresis gel when the gel is placed in the gel processing system. In some embodiments, the at least one light source may comprise or consist of a single lamp light source, a multiple lamp light source, one or more LEDs, or one or more arrays of LEDs. In some embodiments, the at least one light source may emit white light and may include one or more filters that exclude light of undesirable wavelengths from illuminating the gel cassettes in the device. The wavelengths that may be filtered out as undesirable may include those that are not suitable for exciting the relevant light sensitive molecules in a manner to provide a clear signal for the image capture system to identify, or may include wavelengths that overlap with emission beams that are to be imaged.

For example, in some embodiments, the light source may comprise a blue light source, such as a blue LED, a blue lamp, or a white LED or lamp used with a blue filter. The blue light emitted from the blue light source may be in the wavelength range of from about 435 nm to about 500 nm, from about 440 nm to about 490 nm, for example, from about 450 nm to about 475 nm, from about 460 nm to about 470 nm, or about 475 nm. In such an example, the light sensitive molecules that may be used to label a sample or a standard that is being processed on a gel cassette may have an excitation wavelength within the wavelength range of from about 440 nm to about 490 nm, for example, from about 450 nm to about 475 nm, from about 460 nm to about 470 nm or about 475 nm.

In some embodiments, the wavelength range of the light source is within about 20 nm of the maximum excitation wavelength of the light sensitive molecules. It should be understood that any suitable light sensitive molecules may be used and that such light sensitive molecules may have different excitation wavelength ranges than the ranges of blue light exemplified above. In such cases, suitable lamps, LEDs, filters, and other optical components may be used that provide appropriate excitation wavelengths.

In some embodiments, the gel illumination system may include more than one light source. In some embodiments, the gel illumination system may have at least one light source for each running reservoir/gel cassette assembly in the device. In some embodiments, the gel illumination system may include more than one light source for each running reservoir/gel cassette assembly, such as 2-10 light sources, 0.3-8 light sources, or 4-6 light sources. In some embodiments, the light source may comprise an array of LEDs. In such a manner, a single light source may include, for example, from one to 50 LEDs, from two to 40 LEDs, from three to 30 LEDs, from five to 25 LEDs, from six to 20 LEDs, from seven to 18 LEDs, or from eight to 16 LEDs.

In some embodiments, the gel illumination system may include one or more light focusing and/or light manipulating devices that may be associated with all, some, or one of the light sources of the illumination system. In some embodiments, the light focusing or light manipulating devices may be selected from filters, colored filters, neutral density filters, low pass filters, high pass filters, bandpass filters, dichroic filters, mirrors, dichroic mirrors, lenses, collimating lenses, wave plates, wave guides, prisms, defraction gratings, baffles, beam splitters, combinations thereof, and the like. In some embodiments, the light focusing or light manipulating device may comprise a light intensity controlling component. In some embodiments, the light intensity controlling component may comprise a neutral density filter or a voltage controller for controlling the voltage supplied to (and thereby the intensity emitted from) the light source. In some embodiments, controlling the intensity of the light source provides for improved dynamic range over existing gel illumination systems. In some embodiments, the at least one light source may be pre-configured such that no additional manipulation of the gel illumination system and/or the gel processing system is required, beyond automatic or manual activation of the system or a combination of both manual and automatic, to provide sufficient illumination for successful image capture. The configuration may provide image capture at the position at which an electrophoresis gel is placed into the device when the device is being used for electrophoresis.

In some embodiments, the device may include an image capture system that may capture real-time images of a gel during processing and provides the images to a computer control and analysis system of the device. The image capture system may be configured to capture a pre-processing image of electrophoresis gels, prior to initiation of the gel processing, for use by the image analysis system for background subtraction. In some embodiments, the image capture system may comprise a digital camera. In some embodiments, the image capture system comprises a digital camera capable of producing output images of greater than 300 DPI, such as 300 DPI to 3000 DPI, such as 300 DPI to 2600 DPI, such as 400 DPI to 2200 DPI, 400 DPI to 2000 DPI, 500 DPI to 1600 DPI, 500 DPI to 1200 DPI, 500 DPI to 800 DPI, or 500 DPI to 600 DPI. It should be understood that any suitable output image DPI is acceptable, for example, at least 300 DPI. In some embodiments, the image capture system may be configured to provide the captured image in any suitable image file format, for example, as a .pdf file, a TIFF file, or a bitmap file. Similarly, the resolution of the captured image may be greater than about 1 megapixel, for example, from about 1 megapixel to about 6 megapixels, from about 1 megapixel to about 5 megapixels, from about 1.1 megapixels to about 4.5 megapixels, from about 1.2 megapixels to about 4.0 megapixels, from about 1.3 megapixels to about 3.5 megapixels, from about 1.4 megapixels to about 3.2 megapixels, from about 1.5 megapixels to about 3.0 megapixels, from about 1.6 megapixels to about 2.8 megapixels, from about 1.7 megapixels to about 2.5 megapixels, or from 1.8 megapixels to about 2.2 megapixels. It should be understood that any suitable image resolution is acceptable, for example, a resolution of at least about 1 megapixel. In some embodiments, the image capture system may include one or more image focusing or image manipulating devices such as devices selected from filters, mirrors, lenses, and the like.

In some embodiments, the gel electrophoresis device may include at least one image capture system for each running reservoir/gel cassette assembly in the device. In some embodiments, the image capture system includes more than one digital camera for each running reservoir/gel cassette assembly. In some embodiments, the at least one image capture system is configured to capture images at the position at which at least one electrophoresis gel is placed in the device when the device is being used for electrophoresis. In some embodiments, the at least one image capture system is pre-configured such that no additional manipulation of the image capture system is required, beyond automatic or manual activation of the system, to provide successful image capture. The configuration may provide image capture at the position at which an electrophoresis gel is placed into the device when the device is being used for electrophoresis.

In some embodiments, the image capture system may be configured to provide real-time imaging of at least one electrophoresis gel during electrophoresis. In some embodiments the image capture system may be configured to provide real-time imaging of an electrophoresis gel, in a gel cassette assembly, from an initiation of the gel processing through at least completion of the gel processing. In some embodiments, the gel electrophoresis device may be configured to capture an image of an electrophoresis gel in a gel cassette for use as a background subtraction image.

In some embodiments, the gel electrophoresis device include a suitable integrated system display, an integrated computer system or computer processor, and suitable integrated memory to run and store software, and run data, and meet the parameters of controlling the processing, imaging, and analysis of gel cassettes inserted into the device. In some embodiments, the display may display one or more real-time images of gels during the various background image capture, gel processing, image capture, and analysis processes. The display may be any suitable display such a flat screen display or a touch screen display system. In some embodiments, the display system may have a viewable image size to approximate an actual gel size or larger. The display may provide for output of multiple gel images at once, or for output of images of multiple gels at once. The display may comprise a touch screen display through which a user may interact with the device to provide user input such as run data, for example, voltage, current, power, time, and data about the standards being used, to provide manual control of the device or manual input of run protocols. User input may also be provided to provide selection of pre-loaded protocols, selection of pre-loaded standards, or other run information.

In some embodiments, the gel electrophoresis device or the software or firmware may provide for, may include, or may meet one or more of a number of desirable conditions or characteristics. In some embodiments, external interfaces are provided. For example, a USB Host support and file system interface may be provided to support use of a USB stick. A USB Device support and file system interface may be provided to support direct connection to a PC (mass storage device). An FTP server and file system interface may be provided to support network file transfer.

In some embodiments, the gel electrophoresis device or the software or firmware may provide for, may include, or may meet one or more on-board capabilities. For example, the software or firmware may provide output of relative quantitative analysis results including estimated molecular weight, estimated amount, estimated percent purity (band percentage within a lane), and estimated resolution (band/peak width). Internal memory sufficient for storage of at least 100 gel images and their associated data and report files can be provided. Capability of calculating relative molecular weight (MW), quantitation, and purity may be provided. Identification of bands on membranes, based, in part, on image analysis may also be enabled. On board lane and band tracking, based either on image analysis or user input of the relevant information from the gel cassette being used, may also be provided by software or firmware. Multiple relative standard alignment capability for calculating molecular weight over peak position (MW/Rf) for analytes between lanes containing standards, may be provided. An onboard Protein and/or Nucleic Acid Standard Database, some of which may be pre-loaded and some of which may enable a user to add new unique sets of standards, may also be provided. In some embodiments, real-time snapshots of the gel during electrophoresis, shown at a refresh rate of 35 seconds or less, and at a user's request, may be provided. The time of the currently displayed last snapshot was taken may be displayed with the snapshot on the GUI screen. User control over default separation parameters (time, voltage, current) may be provided. User control over image capture parameters (brightness, exposure, contrast, gamma) may be provided. Export of images in TIFF format may be provided. Reports and gel images in image file format may be provided that may be printed directly from a memory device inserted into a photo printer. Field upgrades to onboard software using USB stick interface may be provided. Generation of MS Excel compatible files may be enabled. A re-compute function for editing which lanes, which standards, correct lane numbers, and load quantity used, may be provided. User selection of an image and then automatically pulling associated files for re-processing may be provided as may a user warning when the memory is full. Output files may be provided with a time and date stamp. Output files may be named in such a way as to differentiate multiple runs. Moreover, a display of the most recent output file location may be provided so a user may easily retrieve their data from internal or external storage.

In some embodiments, the gel electrophoresis device or the software or firmware may provide other conditions or characteristics. In some embodiments, a "real-time" image may be generated. For example, a display of "real-time" images of gels during electrophoresis may be provided. One or multiple gel images may be simultaneously displayed side by side on the display. The lane overlay may be displayed horizontally across the top of each gel image, and Rf tracking marks may be displayed vertically along the sides of the gel. The Rf marks may dynamically update, with Rf 1.0 tracking the dye front. Gel images may be presented with black bands on white background or configurable as white bands on a black background. Image display modes may include: a) two gels simultaneous ~80% scale, b) or a single gel at 100% scale. User may select and toggle on thumbnail images for various imaging display modes; thumbnail may highlight what is being shown. The gel image display may be updated as fast as possible, but no more frequently than the image capture rate. A pause option during the run may be used to allow the user to examine the gel image before the run is complete. Initiation of the pause option turns off the power supply to the gel and then allows the user to have the option to collect any relevant data, resume the run, or terminate the run and collect any relevant data.

In some embodiments, the gel electrophoresis device or the software or firmware may provide for, may include, or may meet one or more of the following desirable conditions or characteristics. In some embodiments, automation is provided, for example, one or more of the following: tracking of the dye front with feedback to the run controller to auto stop once the front has advanced as far as desired, configuration to allow for entry of user-defined standards (MW and/or quantity); and incorporation of image noise reduction.

In some embodiments, the gel electrophoresis device or the software or firmware may provide for, may include, or may meet one or more of the following desirable conditions or characteristics associated with method files. Method files may generally be repositories of parameters controlling the gel electrophoresis device, analysis, and report generation. They may consist of user editable fields with default values. The method files in the gel electrophoresis device software may be read by the computer control system to set the imaging and power supply settings for the run. Method files may be available for user definition. In some embodiments, at least 30 files are available. One method file may be used for each run of the device or separate method files may control the runs in separate running reservoirs. Run specific parameters, including voltage, current, stop mode, running buffer, and the like, may be separate from gel specific parameters (standards, lanes, and the like) within a method file. User may set the default rolling disc radius for background subtraction. A user may set the running buffer type. A user may select/input the experiment voltage, current, time, maximum current limit, combination thereof, and the like. A user may select/input run modes, for example, constant power, constant voltage, or constant current. A user may select/input an auto stop mode, for example, comprising run time in minutes, or dye front tracking. A user may opt to select/input from a database, for example, select one lane assignment for a standard. Each gel may independently use its own standard or it may use the standard from a different gel. For instance, in a two running reservoir run, the right gel may select Lane 1 of the left gel to use as a standard for calculation. A user may select/input a load volume of a standard. A user may select/input electropherogram lanes which will be printed. A user may select/input MW chart parameters and data table units (Rf or mm). A user may select/input quantity curve units, for example, ng, µl, or picomoles. A user may select/input a quantity calibration curve, for example, left or right gel. A user may select/input a curve fit type for an MW calibration. A user may select/input reports to print, for example, to select which lanes get electropherogram reports. A user may select/input reports created and options defined in an output report section. A user may specify to copy output files to an external storage device.

In some embodiments, the gel electrophoresis device or the software or firmware may provide for, may include, or may meet one or more of the following desirable conditions or characteristics associated with automatic lane creation. The method may automatically create lanes after acquisition of a gel image. The method may use bar code or printed information from the cassette image to establish lane boundaries, for example Rf=0 may be set by a user or may be identified from the barcode or printed information. Gaps between gels may be identified and prevented from being defined as a lane. Lane numbering may be restarted for each additional gel. Tilt in lanes may be taken into account with the same width at top and bottom of the gel as defined, for example, by a comb, vertically aligned to centroid of bands in lane. A manual selection of an area of interest may be provided for lane creation.

In some embodiments, the gel electrophoresis device or the software or firmware may provide background subtraction after image acquisition. A background image of one or more gels may be captured prior to the start of gel processing, the image may be used for background subtraction. A display electropherogram showing background subtraction may be provided. The electropherogram image for background subtraction purposes may display peak histogram, gel/lane number, background line, and associated gel/lane slice image. The scale of the electropherogram may match the lane image scale and the bands may align with the peaks. Background subtraction may be conducted using a rolling disc method before band detection. The user may adjust the radius for a rolling disc method from 100 to 900 in 100 increments using a rolling value index and up/down arrows. An electropherogram may be displayed for live display of rolling disc adjustment effect after each run. Rolling disc values may be saved in the method file associated with a particular gel. Default rolling disc radius may be set and may be user adjustable. The rolling disc radius may be annotated on electropherogram images and reports, for example, as background subtraction: rolling disc, radius=X. Other suitable background subtraction methods may be supported. Peak numbers, widths or other annotation may be shown. User-selected units from a method file may be shown. Pixel Intensity may be shown. The electropherogram image used for background subtraction adjustment may be from the lane with the most band/peaks as determined with a specific default rolling disc radius, for example, of 800. In some cases, a user may select any other lane from a particular gel to make an adjustment.

In some embodiments, the gel electrophoresis device or the software or firmware may provide band detection sensitivity, for example, to provide adjustment of a band detection threshold. The determination of band detection sensitivity may be configured to iterate until band count stabilizes. Sensitivity may be fixed before gel analysis, for example, with respect to final band detection, electropherogram, Band %, MW determination, and/or quantitation.

In some embodiments, the gel electrophoresis device or the software or firmware may provide for automatic band detection. Correction may be provided for band detection errors. The errors may be directly correctable with the software or may be corrected offline using third party analysis software. The device may be configured such that user adjustment of background subtraction parameters may be made to affect band detection sensitivity. MW and concentration data from standards may be incorporated. One or multiple standards may be used, for each gel, for calculations. A pre-loaded standards database may be used for lanes with standards for establishing the number and location of bands. User defined standards which are not detected correctly may result in a GUI issue warning and correction window for the user. Band numbers within lanes may be displayed in electropherograms and associated with calculations. Band numbering may begin with 1 in each lane closest to Rf=0.

In some embodiments, the gel electrophoresis device or the software or firmware may be configured to provide, calculate, display, and/or print out one or more characteristics associated with peak position, molecular weight (MW), peak height, peak area, peak volume, and band percentage. For example, one or more of the following may be provided: generation of peak position (Rf or mm); molecular weight (MW); peak height (pixel intensities); peak area; peak volume; band sharpness; and band percentage. These characteristics may be provided for every peak. Calculations may be background-subtracted. A display may be provided for peak number, Rf or mm, molecular weight (MW), quantity, band sharpness, and band percentage for every peak. The following parameters may be determined and/or calculated and the numerical values of each band in a selected lane may be presented in table form, graphically displayed, and/or printed out. Peak position (Rf) may be a value between 0.000 and 1.000. MW may be determined using the molecular weights of one or more known gel standards. Peak height may be the background-subtracted peak pixel intensity of a given band. Peak area may be calculated using the following equation (band width is also known as band sharpness): Peak Area=Band Width×Band Length. Peak volume may be calculated using the following equation: Peak Volume=Peak Area×Peak Height. Volumes may be used for band % and mass quantitation. A value for % Purity (Band % per lane) may be calculated using the following equation: % Purity= (Peak Volume of Peak number in lane/Sum of Peak Volumes for Peaks in lane)×100. In some embodiments, the gel electrophoresis device or the software or firmware may generate lane images and electropherograms. An electropherogram of selected lanes may be generated, for example, including lane images and annotations of lane numbers and whether the left or right gel corresponds to the image. The electropherogram's x-axis may be Rf (default) or mm (user selected) with pixel intensity on the y-axis. Rf may range, for example, from 0.0 to 1.0, left to right, in 0.1 increments. Pixel intensities may range, for example from 0 to 255 for a 16-bit grayscale image. Peak numbers may be shown on the electropherogram of a selected lane. Peak boundaries denoting band sharpness may also be shown on the electropherogram. The electropherogram may show a background.

In some embodiments, the gel electrophoresis device or the software or firmware may comprise or be linked to a standards database. This database may comprise a repository for files used by the image analysis software and may be added to or edited by the user. These files may be specified in a run method file.

MW Vs. Rf Chart:

In some embodiments, there may be a pre-defined onboard standards database containing information about MW standards. This information may include the MW for each of multiple sequentially identified bands. This database may be added to by the user. Pre-set standards may be included, for example, saved as read-only. The user may select a standard from the database for each run. A MW "calibration" curve and chart may be generated using pre-existing MW data for standards (pre-loaded or user-defined) after a gel run. This curve and chart may be displayed on the device and may optionally be provided in the report. The chart may be annotated with the gel and lane number as well as with a date and time stamp. This information may be used to generate the standards overlay displayed at the end of the gel run. Curve fitting may be cubic spline, for example, by default. Log MW or other fitting may be selected by the user. The user may select a MW standard from the database, and which lane the standard is in. If no MW standard is identified, MWs cannot be computed, and a device prompt may notify the user.

Relative and Absolute Quantitation:

The pre-defined onboard standards database may include quantities for identified bands. This database may be added to by the user, but some pre-set standards may be read-only. The user may select a standard from the database for each run to be quantitated. This may be configured by the method file. A quantitation "calibration" curve and chart may be generated using pre-existing quantity data for standards after the gel run. The standards may be pre-set or user-defined. The curve and chart may be displayed on the device and may be available for the report. The chart may be annotated with the gel and lane number. Curve fitting for quantitation may be linear or may be selected from a user selected option. The user may select a quantitation standard from the database, and which lane or lanes the standard(s) is/are in. The band may be selected and related to its quantity value. If no quantitation standard is identified, quantities cannot be computed, and a device prompt may be used to notify the user. Some standards may be made such that the software may determine the band from the MW location. One or more, for example, five, fields may be used for quantitation standard. Exemplary fields may include: approximate MW as determined after run; quantity; volume loaded; lane number; and quantitation standard database file. A user may select previously run calibration curves for quantitation or the curve from one or more other gels in the same run. Storage for multiple quantity curves for each gel type may be provided. Curves may be time and date stamped, for example, with gel lot number, running buffer type, gel type, and quantitation standard database selection.

In some embodiments, the gel electrophoresis device or the software or firmware may provide for acquiring an image of a western-transferred membrane. Once acquired, an analysis may be used on the software for MW assignments. This function may include reflective visible and EPI fluorescent light imaging capabilities on the device. A frame may be provided to hold a membrane for imaging. The membrane image may be date and time stamped, and may be associated with the gel from which it was derived. Membrane images may be stored.

In some embodiments, the gel electrophoresis device or the software or firmware may provide for creating an output report. For example, the generation of a raw gel image may be provided at least a 16 bit 300 dpi grayscale uncompressed TIFF file, as a separate output file. The image may comprise lower quality image may be embedded within the report.

Report Generation:

A plurality of selectable report formats may be provided, for example, a default minimal format, a comprehensive format, and a user definable format. Exemplary report sections available for user selection may include: electrophoresis parameters, voltage, current, power, and time (digital and/or graphical); gel image annotating which is left and right from the user perspective; gel band identification marking and lane numbering; standard displayed in red-MW assignment lines with values shown on side overlaid on a gel band identification image; MW calibration curve; calibrated volume curve for quantitation; and calibrated load.

For electropherograms, reports may show "pixel intensity," "Rf" horizontal background subtracted histogram with band numbers shown above peak's, display background level as line, real horizontal image of lane scaled aligned with peaks, background subtraction method, band noise factor and slope (S/N used to determine peak), bar code information (number of wells, gel %, and the like), standard type and assignments, buffer type, voltage, current and run time, illumination mode, folder name (lot, serial number), and power used during the gel run.

In some embodiments, the gel electrophoresis device or the software or firmware may provide a power supply exhibiting an independent output voltage of from about 0 to about 400 V, for example, 335 V. The power supply may have independent output current of from about 0 to about 0.5 A, for example, 375 mA, and output power is from about 0 to about 200 Watts.

In some embodiments, the gel electrophoresis device or the software or firmware may provide for external interfaces: For example, the graphical user interface (GUI) module may comprise an LCD display, a keypad, and/or a touch-screen. The user interface module may control the screens displayed on the LCD. These control operations may be performed by receiving information from the user via the keypad and/or touch-screen and by responding to it via display update and/or delegation of "interpreted" information to other modules in the system. The GUI may be designed so as to not require a pointing device or keyboard. In some embodiments, file transfer between the instrument and a PC may be accomplished in any of a variety of ways, for example, via USB memory stick, via USB cable directly connected to the PC, or via Ethernet network transfer using FTP.

In some embodiments, a combination of one or more of the following user input options may be supplied: initiate run, defined, allowed, enabled, controlled via method files, illumination, abort run, end run, image and analyze, and select report attributes. In some embodiments, the following communications interfaces may be provided: USB Type A interfaces, USB Type B interfaces, and RJ-45 sockets. In some embodiments, the software may have one or more of the following attributes, for example, automation of electrophoresis runs from insertion of the gels through analysis report generation. In some embodiments, multiple types and lanes of MW/concentration standards may be used on the same gel during the same run. In some embodiments, automatic identification and creation of run lanes may be provided based on information about the gel being inserted. In some embodiments, storage of lane templates (either pre-stored or user inputted) may be provided for various gel types/well configurations. In some embodiments, pre-stored information about various existing protein standards, storage of user-input information about protein standards, and MW data editable for protein standards, are provided. In some embodiments, automatic real time detection of bands is provided. In some embodiments, fluorescence calibration generation of a MW vs Rf chart is provided, for example, including calibration and curve fitting, determination of MW based on a standards calibration, determination of purity (band percentage), relative protein quantitation, and absolute protein quantitation. In some embodiments, the features and adjustable parameters that may be provided may include, but are not limited to, generate "real-time" minimum 16-bit color images, save image as TIFF, JPEG, or bitmap, embed gel image (at least 300 dpi resolution) into output, image editing including but not limited to adjustment of brightness, zoom, crop, and the like and provision of annotations, lane boundary editing, lane tilt/warp correction capability, manual band detection, manually select area of interest (gel region, single lane, band), band-detection sensitivity adjustment capability, band editing capability, accommodate different exposure times, and fluorescence/absorbance band detection duality. In some embodiments, the features and adjustable parameters that may be provided may include, but are not limited to, generate and display real-time electropherogram image of the detected bands for each lane including background subtraction, including information such as a display of the lane image with the electropherogram, peak ID/band number in each lane, peak position (pixel, mm, Rf), peak height, peak area and peak volume, peak width & resolution based on band sharpness, peak splitting with Gaussian peak fitting capability, peak normalization (band-to-band, lane-to-lane), electropherogram subtraction, electropherogram overlays on screen, band pattern matching (across gels), comparative accuracy, and reproducibility (MW). In some embodiments, comparative reproducibility (purity), Inter-gel analysis—MW, concentration, mass, and purity, and inter-gel normalization may be provided. In some embodiments, a gel performance/quality confirmation and/or a final background subtracted electropherogram image may be provided. In some embodiments, two-way communication between an NGE instrument and a PC may be provided. In some embodiments, data transfer from an instrument to an external source at the end of a run may be provided. In some embodiments, the features and adjustable parameters that may be provided may include, but are not limited to, read and record gel type (Cat #, lot # and unique identifier) such as from a barcode or from a gel image, touch-screen GUI, software updating capability and functions, data table generation (for example, EXCEL formatted), generate and print report format/layout (for example, MS WORD), Link to other files (import/export functions), Print, high resolution image (at least 300 dpi), operating System compatibility (for example, with WINDOWS), exportable (for example, to EXCEL) table files, pre-loaded printer drivers, print capability without a PC, and macro writing capability.

All publications, patents, and patent applications mentioned in this specification are herein incorporated by reference to the same extent as if each individual publication, patent, or patent application was specifically and individually indicated to be incorporated by reference.

While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A gel electrophoresis device comprising:
a housing;
a gel processing system said gel processing system comprising at least one, optionally more than one, gel holder configured to hold a gel cassette in a vertical orientation, and at least one, optionally more than one, buffer reservoir;
a gel illumination system;
an image capture system, said image capture system being configured to provide real time imaging of at least one electrophoresis gel during an electrophoresis run, wherein said real-time imaging comprises simultaneously imaging a gel, visible or fluorescent bands, and migration of the visible or fluorescent bands; and
an image analysis system;
wherein the gel processing system, the gel illumination system, the image capture system, and the image analysis system are all housed within the housing, and wherein the systems are operably associated and automated.

2. The device of claim 1, wherein the gel processing system comprises at least two gel buffer reservoirs, at least two gel holders, and at least one anode and at least one cathode for each of the at least two gel holders.

3. The device of claim 1, wherein the gel illumination system comprises at least one light source configured to illuminate at least one electrophoresis gel when the gel is placed in the gel processing system.

4. The device of claim 3, wherein the at least one light source comprises at least one blue light source.

5. The device of claim 4, wherein the at least one blue light source emits blue light in a wavelength range of from about 440 nm to about 490 nm.

6. The device of claim 3, wherein the at least one blue light source comprises at least one LED blue light source.

7. The device of claim 3, wherein the at least one light source comprises at least two light sources.

8. The device of claim 3, further comprising at least one light intensity controlling component.

9. The device of claim 3, wherein the at least one light source is pre-configured such that no additional manipulation of the gel illumination system is required, beyond automatic or manual activation of the system, to provide sufficient illumination for successful image capture at the position at which an electrophoresis gel is placed into the device when the device is being used for electrophoresis.

10. The device of claim 1, wherein the image capture system comprises at least one digital camera.

11. The device of claim 10, wherein the at least one digital camera is pre-configured such that no additional manipulation of the image capture system is required, beyond automatic or manual activation of the system, to provide successful image capture at the position at which an electrophoresis gel is placed into the device when the device is being used for electrophoresis.

12. A method of performing gel electrophoresis comprising:
performing electrophoresis on at least one labeled sample in a gel electrophoresis device according to claim 1; and
imaging in real-time the at least one labeled sample with the image capture system;
wherein at least the performing and imaging steps are operably associated with each other and automated.

13. The method of claim 12, further comprising forming an analyzed image by analyzing the imaged sample with an image analysis system operably associated with the image capture system.

14. The method of claim 13, further comprising printing a hard copy of the analyzed image.

15. The method of claim 12, further comprising electrophoresing a labeled protein standard simultaneously with the labeled sample.

16. The method of claim 12, further comprising determining the absolute amount of at least one labeled protein in the sample.

17. The method of claim 12, wherein the method is performed in less than about 30 minutes.

18. The method of claim 12, wherein the method is performed in less than about 15 minutes.

19. The method of claim 12, wherein the imaging comprises exposing the labeled sample to at least one blue light source LED blue light source.

20. The method of claim 19, wherein the at least one LED blue light source emits blue light in a wavelength range of from about 440 nm to about 490 nm.

21. The device of claim 1, wherein the image capture system is configured to image the migration of the visible or fluorescent bands during an electrophoresis run from the point of introduction of one or more samples to an electrophoresis gel through generation of a report of results.

* * * * *